United States Patent [19]

Lebenthal

[11] Patent Number: 5,120,539
[45] Date of Patent: Jun. 9, 1992

[54] AMYLASE-ELECTROLYTE ORAL REHYDRATION METHOD AND COMPOSITION

[75] Inventor: Emanuel Lebenthal, Haverford, Pa.

[73] Assignee: Doyle W. Boatwright, Phoenix, Ariz.; a part interest

[21] Appl. No.: 643,414

[22] Filed: Jan. 22, 1991

[51] Int. Cl.⁵ .................... A61K 35/78; A61K 47/00; C12P 19/14; A23L 1/10
[52] U.S. Cl. .................... 424/195.1; 426/28; 514/777; 514/778; 514/867; 435/99; 435/105
[58] Field of Search ........... 426/28; 424/195.1; 514/777, 778, 867; 435/99, 105

[56] References Cited

U.S. PATENT DOCUMENTS

| | | | |
|---|---|---|---|
| 4,307,194 | 12/1981 | Frommer | 435/122 |
| 4,376,129 | 3/1983 | Piurovich | 426/64 |
| 4,565,702 | 1/1986 | Morley | 426/93 |
| 4,927,654 | 5/1990 | Barnett | 426/548 |
| 4,942,042 | 7/1990 | Bhargava | 424/683 |

OTHER PUBLICATIONS

Alam, A. N. Hydrolyzed Wheat Based Oral Rehydration Solution for Acute Diarrhoea, Arch Disease in Childhood 1987 62, 440-444.
Molla, A. M. Food Based Oral Rehydration Salt Solution for Acute Childhood Diarrhoea, The Lancet Aug. 19, 1989 pp. 429-431 vol. II #8660.
Khin-Maung-U, Cereal Based Oral Rehydration Therapy I. J of Pediatrics Apr. 1991 vol. 118 #4 Part 2.
Greenough W B Cereal Based Oral Rehydration Therapy II. J of Pediatrics Apr. 1997 vol. 118 #4 Part 2.
Khin-Maung-U, Cereal Based . . . Discussion IV J of Pediatrics Apr. 1991 vol. 118 #4 Part 2.

Primary Examiner—Ronald W. Griffin
Assistant Examiner—Ralph Gitomer
Attorney, Agent, or Firm—Tod R. Nissle

[57] ABSTRACT

A method for treating diarrhea in children. The method boils in water a natural source of complex carbohydrates and processes the resulting aqueous solution of complex carbohydrates to produce an aqueous solution of dextrorotatory polysaccharides having a desired osmolarity and electrolyte concentration.

24 Claims, No Drawings

AMYLASE-ELECTROLYTE ORAL REHYDRATION METHOD AND COMPOSITION

This invention relates to methods and compositions for treating diarrhea.

More particularly, the invention relates to a process which effectively replaces fluid lost by a child in stools due to diarrhea and which effectively decreases stool volume.

Chronic diarrhea, and the dehydration, malnutrition, vitamin deficiencies, and weakened immune system which accompany chronic diarrhea are the main causes of infant mortality and morbidity. One-third of the deaths in children younger than five (5) years of age are associated with diarrhea, and worldwide the disease kills about four million (4,000,000) children each year.

Oral rehydration therapy can prevent death from fluid loss and is especially effective when administered at the earliest stage of any diarrhea illness. The standard oral rehydration solution (SORS) consists of 3.5 grams sodium chloride, 2.5 grams sodium bicarbonate (90 mEq/L sodium), 1.5 grams potassium chloride, and 20 grams glucose dissolved in one liter of water. One important disadvantage to SORS is its apparent lack of efficacy in reducing diarrhea. SORS replaces fluid lost in stools but does not decrease stool volume and may even increase it. If choronic diarrhea continues, a child can die a slow and horrible death due to the malnutrition, vitamin deficiencies, and weakened immune system which accompany the diarrhea, even while the child is receiving SORS.

Further, in many developing countries, supplies of SORS are limited so that a child may only receive the benefits of a few feedings before the SORS is no longer available.

Accordingly, it would be highly desirable to provide an improved method and composition which would replace fluids lost during diarrhea while significantly reducing the volume of the stool produced by an infant with diarrhea.

Therefore, it is a principal object of the invention to provide an improved method and composition which would replace electrolytes lost during diarrhea, reduce the volume of stool produced by a child with diarrhea, and likely save the lives of many children throughout the world.

Briefly, I have discovered a process for treating in a child chronic diarrhea, along with the dehydration, malnutrition and intestinal mucosal injury attendant the chronic diarrhea. The process includes the steps of boiling in water a source of complex carbohydrates $(C_6H_{10}O_5)x$ selected from the class consisting of potatoes, arrowroot, tapioca root, corn, wheat, rice, oats, barley, and beans to form an aqueous solution of complex carbohydrates removed from said source during boiling, the aqueous solution of complex carbohydrates having an selected osmolarity. The aqueous solution of complex carbohydrates is subjected to action by at least one in the class of reactants comprising heat, acids and enzymes to hydrolyze the complex carbohydrates and produce water soluble dextrorotatory polysaccharides, to increase the osmolarity of the solution to a value between about 200 and 300, and to produce a pH of the solution in the range of one to nine. After the aqueous solution has been subjected to action by a reactant, the solution is ingested by an infant. When the solution passes from the stomach of the infant to the small intestine of the infant, glucoamylase is combined with the solution. If desired, glucoamylase can be injected into the small intestine with a needle and feeding tube.

The water soluble dextrorotatory polysaccharides produced during the hydrolysis of the complex carbohydrates preferably are short chain glucose polymers comprising two to nine glucose units. I have discovered that such short-chain glucose polymers are hydrolyzed and absorbed in the small intestine faster than isocaloric Dglucoamylase. After short-chain glucose polymers are ingested by a child, they preferably are hydrolyzed by glucoamylase in situ for absorption by the intestinal tract the child. The glucoamylase can be ingested with or after the short-chain glucose polymers or can comprise the glucoamylase which was present in the small intestine of the child prior to ingestion of the dextrorotatory polysaccharide short-chain glucose polymers. The glucoamylase preferably does not combine or mix with the short-chain glucose polymers until after the short-chain glucose polymers enter the small intestine. The osmolarity of the short-chain glucose polymers on entering the small intestine is believed to help reduce stool volume.

When alpha-amylase is the reactant utilized to hydrolyze the complex carbohydrates in an aqueous solution to form dextrorotatory polysaccharides or dextrins, the thermal stability of the amylase is improved by the presence of 2000 to 5000 parts per million sodium chloride or by 200 to 400 parts per million calcium in the aqueous solution of complex carbohydrates. Improving the thermal stability of the amylase is important in the practice of the invention because it enables the amylase to be utilized at higher temperatures which are closer or comparable to the temperatures utilized to boil complex carbohydrate sources to release complex starch carbohydrates into aqueous solution to be acted on by heat, acids, or enzymes.

Whether complex carbohydrates in aqueous solution are acted on by a heat, acid, or enzyme reactant, the resulting dextrorotatory polysaccharides provide a high caloric density aqueous solution while contributing to the curtailment of stool volume in an infant. While the exact mechanism which causes the process of the invention to curtail diarrhea is not known, it is theorized that the molecule size of the dextrorotatory polysaccharides and the osmolarity which they produce in comparison to SORS tends to inhibit the passage of stool while providing a caloric intake which is readily digested and absorbed by children, even by infants less than six months in age.

The pH of the aqueous solution of dextrorotatory polysaccharides is in the range of one to nine. The pH can be any desired value which will not significantly harm the intestinal tract of the infant, will not facilitate the production of diarrhea, and, importantly, which will not adversely effect the action of heat, acid or enzyme reactants on the complex carbohydrates to produce the dextrorotatory polysaccharides.

The time required for the heat, acids or enzymes to act on the dextrorotatory polysaccharides is three hours or less, preferably less than one hour. This time can be achieved by varying the quantities of heat, acids or enzymes used in respect to the final concentration of dextrorotatory polysaccharides desired in the final aqueous solution. Further, it is preferred that most, if not all, of the complex carbohydrates in the aqueous solution be hydrolyzed into the desired dextrorotatory polysaccharides.

Similarly, the time required to heat a source of complex carbohydrates in water to remove complex carbohydrates from the source into solution with the water can vary depending on the concentration of complex carbohydrates desired. The time required can be reduced by introducing the complex carbohydrate source into the water in powder form.

The following examples depict the presently preferred embodiments of the invention for the purpose of illustrating the practice thereof and not by way of limitation of the scope of the invention. In the examples, all proportions are by weight, unless otherwise noted.

EXAMPLE 1

A dextrorotatory polysaccharide solution is prepared. An aqueous solution of complex carbohydrates is formed by boiling 50 grams of shredded potato in several hundred milliliters of water for thirty minutes and then cooling the water to 40° C. to 50° C. (If at this point sufficient water were to be added to the 40° C. to 50° C. water to increase the volume of the solution to one liter, the osmolarity of the one liter solution typically would be less than 200.) 3.5 grams NaCl (90 mmol/L Na), 2.5 gram sodium bicarbonate (30 mmol/L bicarbonate), 1.5 gram KCl (20 mmol/L K) and 0.01 gram Tenase-1200 alpha amylase is stirred into the aqueous solution. The resulting mixture is allowed to settle at room temperature for twenty to thirty minutes and water is added to increase the volume of the mixture to one liter. The osmolarity of the one liter mixture is 250, can be in the range of about 200 to 300, and is always less than the osmolarity of the SORS. The amount of NaCl utilized in the one liter of aqueous carbohydrate solution can be in the range of 1.0 grams to 5.0 grams; of sodium bicarbonate in the range of 1.0 to 5.0 grams; of KCl in the range of 0.25 to 5.0 grams; and, of Tenase-1200 in the range of 0.0025 to 0.10 grams. Tenase-1200 is a product of Solvay Enzymes, Inc.

EXAMPLE 2

A dextrorotatory polysaccharide solution is prepared according to EXAMPLE 1, except 50 grams of cornstarch is utilized in place of the potato.

EXAMPLE 3

A dextrorotatory polysaccharide solution is prepared according to EXAMPLE 1, except 50 grams of ground wheat is utilized in place of the potato.

EXAMPLE 4

A dextrorotatory polysaccharide solution is prepared according to EXAMPLE 1, except 50 grams of rice powder is utilized in place of the potato.

EXAMPLE 5

A test group of eighteen (18) infants suffering from acute watery diarrhea are treated. Each of the infants is about four months old and each is suffering from shigella bacteria which injure the mucosal linings of the intestinal tract of the infant.

Four of the infants from the test group are selected for a first course of treatment. The length of the first course of treatment is eight (8) hours. Two of the infants are female, two are male. The two female infants each weigh about twelve (12) pounds. The two male infants each weigh about thirteen (13) pounds. Each infant is a member of the Caucasian race. The infants are kept comfortably clothed and warm.

For the initial three (3) hour period each infant is provided with and ingests two (2) ounces an hour of an ISOMIL soybean milk substitute formula and the stool volume of each child is monitored to determine the average stool volume per hour produced by the infant. At the end of the three (3) hour period, each infant is, for a two (2) hour intermediate period, given and ingests two (2) ounces an hour of a standard oral rehydration solution (SORS) consisting of 3.5 grams of sodium chloride, 2.5 grams of sodium bicarbonate (90 mEq/L sodium), 1.5 grams of potassium chloride, and 20 grams of glucose dissolved in one liter of water. During the two (2) hour period the stool of each infant is monitored to determine the average stool volume per hour produced by the child. Following the two (2) hour period during which the four (4) infants are given the standard oral rehydration solution, the infants are, for the final three (3) hours, each provided with and ingest two (2) ounces of ISOMIL per hour and the stool volume of each infant is monitored to determine the average stool volume per hour. During the eight (8) hour first course of treatment, the average stool volume per hour for each infant remains about the same.

Six other infants from the first test group are selected for a second course of treatment. The length of the second course of treatment is eight (8) hours. Three of the infants are female, three are male. The three female infants each weigh about twelve (12) pounds. The three male infants each weigh about thirteen (13) pounds. Each infant is a member of Caucasian race. The infants are kept comfortably clothed and warm. For the initial three (3) hour period each infant is provided with and ingests two (2) ounces an hour of an ISOMIL soybean milk substitute formula and the stool volume of each child is monitored to determine the average stool volume per hour produced by the infant. At the end of three (3) hour period, each infant is, for a two (2) hour intermediate period, given and ingests two (2) ounces an hour of the dextrorotatory polysaccharide solution of EXAMPLE 1. During the two (2) hour period the stool of each infant is monitored to determine the average stool volume per hour produced by the infant. At the end of the two (2) hour intermediate period, each infant is, for the final three (3) hour period, provided with and ingests two (2) ounces of ISOMIL per hour and the stool volume of each infant is monitored to determine the average stool volume per hour. During the final three (3) hour period the stool of each infant is monitored to determine the average stool volume per hour produced by the infant. During the intermediate two (2) hour period, the stool volume decreases by about 30% in comparison to the stool volume of each infant during the initial three (3) hour period. During the final three (3) hour period, the stool volume of each infant is about 30% less than the stool volume of each infant during the initial three (3) hour period.

The remaining eight (3) infants in the first test group are selected for a third course of treatment. The length of the third course of treatment is eight (8) hours. Four (4) of the infants are female, four (4) are male. The four (4) female infants each weigh about twelve (12) pounds. The four (4) male infants each weigh about thirteen (13) pounds. Each infant is a member of the Caucasian race. The infants are kept comfortably clothed and warm. For the initial three (3) hour period each infant is provided with and ingests two (2) ounces an hour of an ISOMIL soybean milk substitute formula and the stool volume of each child is monitored to determine the average stool volume per hour produced by the infant. At the end of the initial three (3) hour period, each infant is, for the remaining five (5) hours, given and ingests two (2) ounces an hour of a standard oral rehydration solution consisting of 3.5 grams of sodium chloride, 2.5 grams of sodium bicarbonate (90 mEq/L sodium), 1.5 grams of potassium chloride, and 20 grams of glucose dissolved in one liter of water. During the remaining five (5) hour period, the stool produced by each infant is monitored to determine the average stool volume per hour produced by the child. During the eight hour course of treatment, the average stool volume per hour for each of the eight (8) infants remains about the same.

EXAMPLE 6

A second test group of eighteen (18) infants is divided into groups of four (4), six (6) and eight (8) and subjected to the first, second, and third, respectively, courses of treatment described in EXAMPLE 2. The second test group is generally equivalent to the first test group in terms of age, weight, sex, and race, except that the second test group is suffering from acute watery diarrhea due to a virus. The results of the second test group are similar to those of the first group. The six (6) members of the second test group which ingest the dextrorotatory polysaccharide solution of EXAMPLE 1 experience about a 20% to 30% decrease in stool volume during the last five (5) hours of their eight (8) hour course of treatment.

EXAMPLE 7

EXAMPLE 5 is repeated, except that during the second course of treatment four (4) ounces of the solution of EXAMPLE 2 is utilized in place of the solution of EXAMPLE 1. Similar results are obtained.

EXAMPLE 8

EXAMPLE 5 is repeated, except that during the second course of treatment four (4) ounces of the solution of EXAMPLE 3 is utilized in place of the solution of EXAMPLE 1. Similar results are obtained.

EXAMPLE 9

EXAMPLE 5 is repeated, except that during the second course of treatment four (4) ounces of the solution of EXAMPLE 4 is utilized in place of the solution of EXAMPLE 1. Similar results are obtained.

EXAMPLE 10

EXAMPLE 9 is repeated, except that at the end of each hour during the first, second, and third courses of treatment, a blood test is performed on each infant to determine the level of glucose in the blood to determine if the intestinal tract of each infant is absorbing sugar from the ISOMIL, standard electrolyte solution, and/or the dextrorotatory polysaccharide solution. In the first test course (four (4) infants) in EXAMPLE 9, the blood sugar level was lower than normal and generally was unchanged during the entire eight (8) hour test course. In the second test course (six (6) infants) in EXAMPLE 9, the blood sugar level during the intermediate two (2) hour period was about 20% greater than the blood glucose level during the initial three (3) hour period of the second test course. During the third test course (eight (8) infants) in EXAMPLE 9, the blood glucose level during the entire eight (8) hour period was lower than normal and remained generally unchanged.

EXAMPLE 11

EXAMPLE 8 is repeated, except that at the end of each hour during the first, second, and third courses of treatment, a blood test is performed on each infant to determine the level of sugar in the blood to determine if the intestinal tract of each infant is absorbing sugar from the ISOMIL, SORS, and/or the dextrorotatory polysaccharide solution. In the first test course (four (4) infants) in EXAMPLE 8, the blood sugar level was lower than normal and generally was unchanged during the entire eight (8) hour test course. In the second test course (six (6) infants) in EXAMPLE 8, the blood sugar level during the intermediate two (2) hour period was about 20% greater than the blood sugar level during the initial three hour period of the second test course. During the third test course (eight (8) infants) in EXAMPLE 8, the blood glucose level during the entire eight (8) hour period was lower than normal and remained generally unchanged.

EXAMPLE 12

EXAMPLE 7 is repeated, except that the blood sugar tests of EXAMPLE 11 are utilized during EXAMPLE 7. Results similar to those in EXAMPLE 11 are obtained.

EXAMPLE 13

A test group of twelve (12) children suffering from acute watery diarrhea are treated. Each of the children is about four (4) years old and each is suffering from a shigella bacteria which has injured the mucosal linings of their intestinal tracts. Four (4) of the children from the test group are selected for a first course of treatment. The length of the first course of treatment is eight (8) hours. Two (2) of the four children are female, two are male. The two (2) female children each weigh about thirty (30) pounds. The two (2) male children weight about thirty-six (36) pounds. During the first course of treatment the four (4) children are each provided with and ingest eight (8) ounces an hour of the SORS described in EXAMPLE 5. During the eight (8) hour period the stool of each child is monitored to determine the average stool volume per hour produced by the child. During the eight (8) hour course of treatment, the average stool volume per hour for each child remains about the same.

The eight (8) remaining children in the test group are selected for a second course of treatment. The length of the second course of treatment is eight (8) hours. Four (4) of the eight (8) children are female, four (4) are male. The four (4) female children each weigh about thirty (30) pounds. The four (4) male children each weigh about thirty-six (36) pounds. During the second course of treatment the eight (8) children are each provided with ingest eight (8) ounces of hour of the dextrorotatory polysaccharide solution of EXAMPLE 1. During the eight (8) hour period of the second course of treatment the stool of each child is monitored to determine the average stool volume per hour produced by the infant. Over the eight (8) hour period, the volume of stool produced by the children during the second course of treatment gradually decreases, until the volume of stool produced during the seventh (7th) and eighth (8th) hours is about 30% less than the volume of stool producing during the first hour of the second course of treatment.

EXAMPLE 14

EXAMPLE 13 is repeated, except that in the second course of treatment eight (8) ounces per hour of the solution of EXAMPLE 2 is utilized in place of the solution of EXAMPLE 1. Similar results are obtained.

EXAMPLE 15

EXAMPLE 13 is repeated, except that in the second course of treatment eight (8) ounces per hour of the solution of EXAMPLE 3 is utilized in place of the solution of EXAMPLE 1. Similar results are obtained.

EXAMPLE 16

EXAMPLE 13 is repeated, except that in the second course of treatment eight (8) ounces per hour of the solution of EXAMPLE 4 is utilized in place of the solution of EXAMPLE 1. Similar results are obtained.

EXAMPLE 17

A dextrorotatory polysaccharide solution is prepared. An aqueous solution of complex carbohydrates is formed by boiling fifty (50) grams of rice powder in several hundred milliliters of water for thirty (30) minutes and adding sufficient water to increase the volume of the aqueous solution of complex carbohydrates to about one (1) liter. The osmolarity of the one (1) liter mixture is less than about two hundred (200). The one (1) liter mixture is then boiled vigorously for thirty (30) minutes to slightly scorch complex starch carbohydrates in the mixture and produce dextrin dextrorotatory polysaccharides. The mixture is cooled to room temperatures. The osmolarity of the cooled aqueous solution of dextrorotatory polysaccharides is 220 mOSm per liter of one (1) calorie per cubic centimeter of food.

EXAMPLE 18

EXAMPLE 5 is repeated except that during the second course of treatment four (4) ounces of the 220 osmolarity solution of EXAMPLE 17 is utilized in place of the solution of EXAMPLE 1. Similar results are obtained.

EXAMPLE 19

EXAMPLE 13 is repeated, except that in the second course of treatment eight (8) ounces per hour of 220 osmolarity solution of EXAMPLE 17 is used in place of the solution of EXAMPLE 1. Similar results are obtained.

EXAMPLE 20

A test group of four (4) infants suffering from chronic water diarrhea was treated. Each of the infants was about four (4) months old and was producing a known stool volume per hour due to the diarrhea. Two (2) of the infants were female, two (2) were male.

Each of the infants was given rice water. The rice water was produced by boiling rice in the water. The rice water reduced the stool volume per hour of each child.

The particular combination of electrolytes and heat, acid or enzyme reactants utilized in the invention and described in the foregoing examples appears particularly useful in producing desired dextrorotatory polysaccharides from complex carbohydrates and in reducing the stool volume of children suffering from diarrhea. Further, electrolyte--reactant packets used in the invention can be inexpensively produced and packaged and used by families in underdeveloped countries. It is believed that electrolyte--reactant packets produced in accordance with the invention may save the lives of literally thousands of children throughout the world.

Having described my invention in such terms as to enable those skilled in the art to understand and practice it, and having identified the presently preferred embodiments thereof, I Claim:

1. A method of treating diarrhea in an infant under six (6) months of age comprising
   (a) administering to the stomach of the infant an aqueous solution of alpha amylase and short chain glucose polymers comprising two to nine glucose units, said aqueous solution being prepared by
      (i) boiling in water a source of complex carbohydrates $(C_6H_{10}O_5)_x$ selected from the group consisting of potatoes, arrowroot, tapioca root, corn, wheat, rice, oats, barley, and beans to form an aqueous solution of complex carbohydrates removed from said source by the heat water during boiling, and
      (ii) subjecting said aqueous solution of complex carbohydrates to action by alpha amylase in situ to hydrolyze said complex carbohydrates and produce water soluble short chain glucose polymers comprising two to nine glucose units; and,
   (b) when said solution passes from the stomach of the infant to the small intestine of the infant, combining in the small intestine glucoamylase with said solution.

2. The method of claim 1 wherein the osmolarity of said solution is in the range of about 200 to 300 mOSm liter of one (1) calories per cubic centimeter of food.

3. The method of claim 1 wherein the pH of said solution is in the range of 1 to 9.

4. The method of claim 2 wherein the pH of said solution is in the range of 1 to 9.

5. The method of claim 2, wherein said aqueous solution further comprises 2000 to 5000 parts per million NaCl.

6. The method of claim 2, wherein said aqueous solution further comprises 200 to 400 parts per million Ca.

7. The method of claim 1 wherein said amylase is present in said aqueous solution in amount of about 0.0025 to 0.10 grams per liter of solution.

8. A process for preparing a diarrhea treatment product for an infant under six (6) months of age comprising:
   (a) boiling in water a source of complex carbohydrates $(C_6H_{10}O_5)_x$ selected from the group consisting of potatoes, arrowroot, tapioca root, corn, wheat, rice, oats, barley, and beans to form an aqueous solution of complex carbohydrates removed from said source by the heated water during boiling, and
   (b) subjecting said aqueous solution of complex carbohydrates to action by alpha amylase in situ to hydrolyze said complex carbohydrates and produce water soluble short chain glucose polymers comprising two to nine glucose units.

9. The method of claim 8 wherein said aqueous solution has an osmolarity in the range of 200 to 300 mOSm liter of one (1) calories per cubic centimeter of food.

10. The method of claim 8 wherein said aqueous solution has a pH is in the range of 1 to 9.

11. The method of claim 9 wherein said aqueous solution has a pH is in the range of 1 to 9.

12. The method of claim 8, wherein said aqueous solution further comprises 2000 to 5000 parts per million NaCl.

13. The method of claim 9, wherein said aqueous solution further comprises 2000 to 5000 parts per million NaCl.

14. The method of claim 8, wherein said aqueous solution further comprises 200 to 400 parts per million Ca.

15. The method of claim 9, wherein said aqueous solution further comprises 200 to 400 parts per million Ca.

16. The method of claim 8 wherein said amylase is present in said aqueous solution in amounts of about 0.0025 to 0.10 grams per liter.

17. A process for preparing a diarrhea treatment product comprising
    (a) preparing a packet containing alpha amylase and a source of at least one electrolyte selected from the group of electrolytes consisting of sodium, potassium and chlorine;
    (b) heating in water a source of complex carbohydrates (C6H10O5)x selected from the group consisting of potatoes, arrowroot, tapioca root, corn, wheat, rice, oats, barley, and beans to form an aqueous solution of complex carbohydrates removed from said source by the heated water;
    (c) adding said amylase and electrolyte source in said packet to said water to subject said aqueous solution of complex carbohydrates to action by said alpha amylase in situ to hydrolyze said complex carbohydrates and produce water soluble short chain glucose polymers comprising two to nine glucose units.

18. The method of claim 17, wherein said packet includes a quantity of NaCl sufficient to form a concentration of 2000 to 5000 parts per million in said aqueous solution.

19. The method of claim 17, wherein said packet includes a quantity of Ca sufficient to form a concentration of 200 to 400 parts per million in said aqueous solution.

20. The method of claim 17 wherein said amylase is present in said water in amounts of about 0.0025 to 0.10 grams per liter of water.

21. A composition for treating diarrhea in a patient and comprising
    (a) a heated aqueous solution of complex carbohydrates (C6H10O5)x; and,
    (b) alpha amylase present in said aqueous solution in amount of about 0.0025 to 0.10 grams of amylase per liter of aqueous solution;
    said aqueous solution being prepared by heating in water a source of complex carbohydrates (C6H10O5)x selected from the group consisting of potatoes, arrowroot, tapioca root, corn, wheat, rice, oats, barley, said alpha amylase acting on said complex carbohydrates to form short chain glucose polymers comprising two to nine glucose units, said composition being ingested by the patient after said alpha amylase has action on said complex carbohydrates to form short chain glucose polymers.

22. The anti-diarrhea composition of claim 21, including a salt present in said aqueous solution in amounts of about 1.0 to 5.0 grams per liters of aqueous solution.

23. The anti-diarrhea composition of claim 21, including calcium present in said aqueous solution in amounts of about 200 to 400 parts per million by weight.

24. An article of manufacture for use in treating diarrhea in a patient, said article of manufacture comprising
    (a) a sealed packet;
    (b) a composition in said packet comprising
        (i) alpha amylase, and,
        (ii) a source of at least one of the electrolytes selected from the group consisting of sodium chloride, potassium chloride, and sodium bicarbonate.
    said sealed packet being opened and said composition being admixed with an aqueous solution of complex carbohydrates to form an anti-diarrhea solution of short chain glucose polymers comprising two to nine glucose units, said anti-diarrhea solution being ingested by the patient to treat diarrhea.

* * * * *